United States Patent [19]

Chaikin et al.

[11] 4,129,250
[45] Dec. 12, 1978

[54] RELATIVE HUMIDITY CONTROL

[75] Inventors: Malcolm Chaikin, Centennial Park; Mstislav S. Nossar, Peakhurst, both of Australia

[73] Assignee: Unisearch Limited, Australia

[21] Appl. No.: 774,014

[22] Filed: Mar. 3, 1977

[30] Foreign Application Priority Data

Mar. 2, 1976 [AU] Australia .............................. PC5071

[51] Int. Cl.² .......................................... G05D 22/02
[52] U.S. Cl. .................................... 236/44 A; 73/77; 73/338
[58] Field of Search ................. 236/44 R, 44 A, 44 E; 73/77, 338, 338.3, 338.6

[56] References Cited

U.S. PATENT DOCUMENTS

| | | | |
|---|---|---|---|
| 2,128,176 | 8/1938 | Bast | 236/44 A |
| 2,504,278 | 4/1950 | Read | 236/44 A |
| 2,754,063 | 7/1956 | Kersten | 236/44 A |
| 2,935,009 | 5/1960 | Cloud | 236/44 A |
| 3,603,135 | 9/1971 | Kawaguchi | 73/77 X |

*Primary Examiner*—Clarence R. Gordon

[57] ABSTRACT

Apparatus for measuring and controlling the relative humidity of exhaust air from an industrial drier in which exhaust air is passed across a dry bulb and a wet bulb thermocouple from which a voltage is derived providing a measure of the relative humidity in the air in the sample. This voltage is used to control the amount of exhaust air from the drier to atmosphere. The wet bulb thermocouple is cyclically dipped in a bowl of water under the control of a timer system of the voltage to control the amount of exhaust air discharged until the wet bulb thermocouple is equilibrated with the exhaust air sampled after dipping.

4 Claims, 2 Drawing Figures

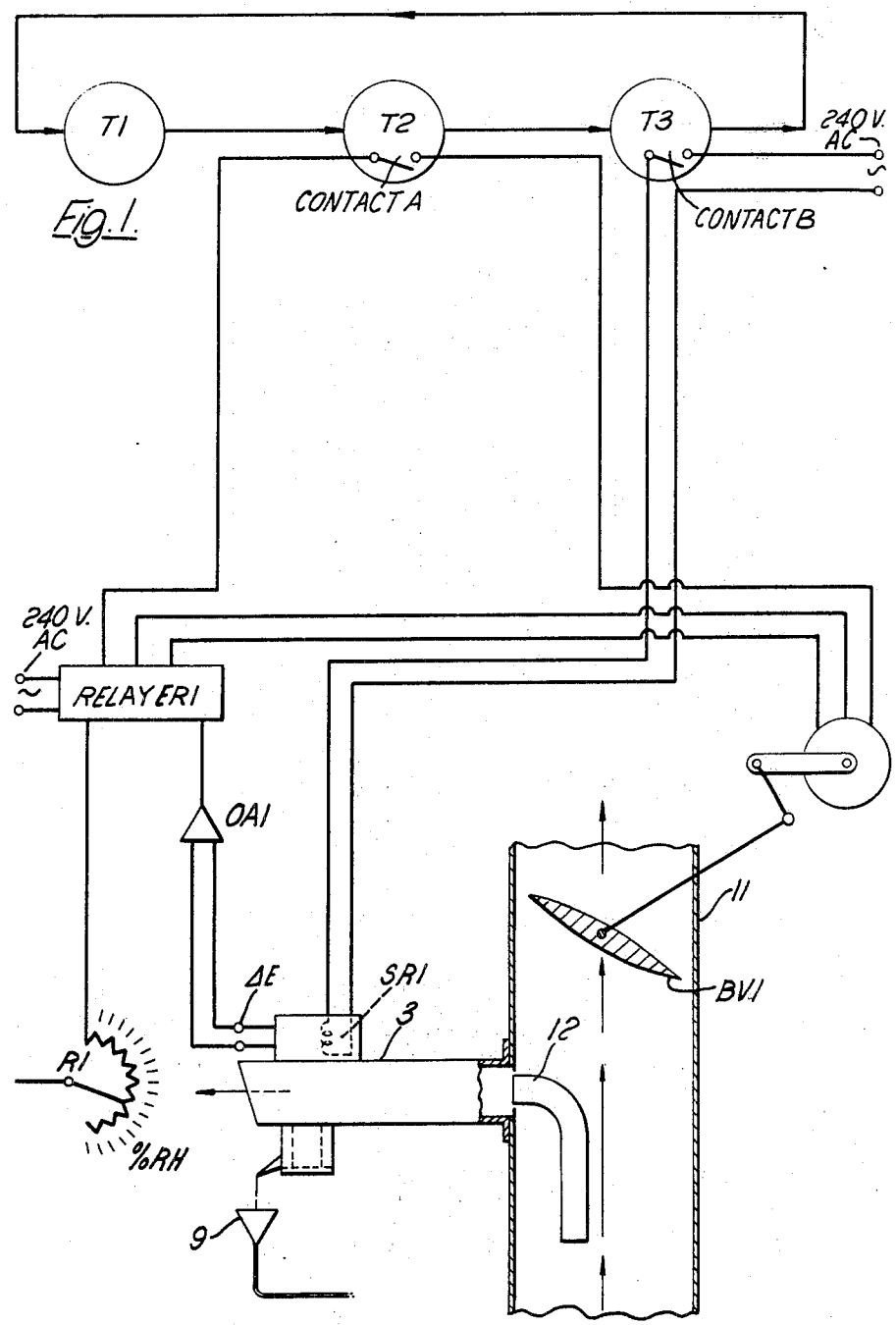

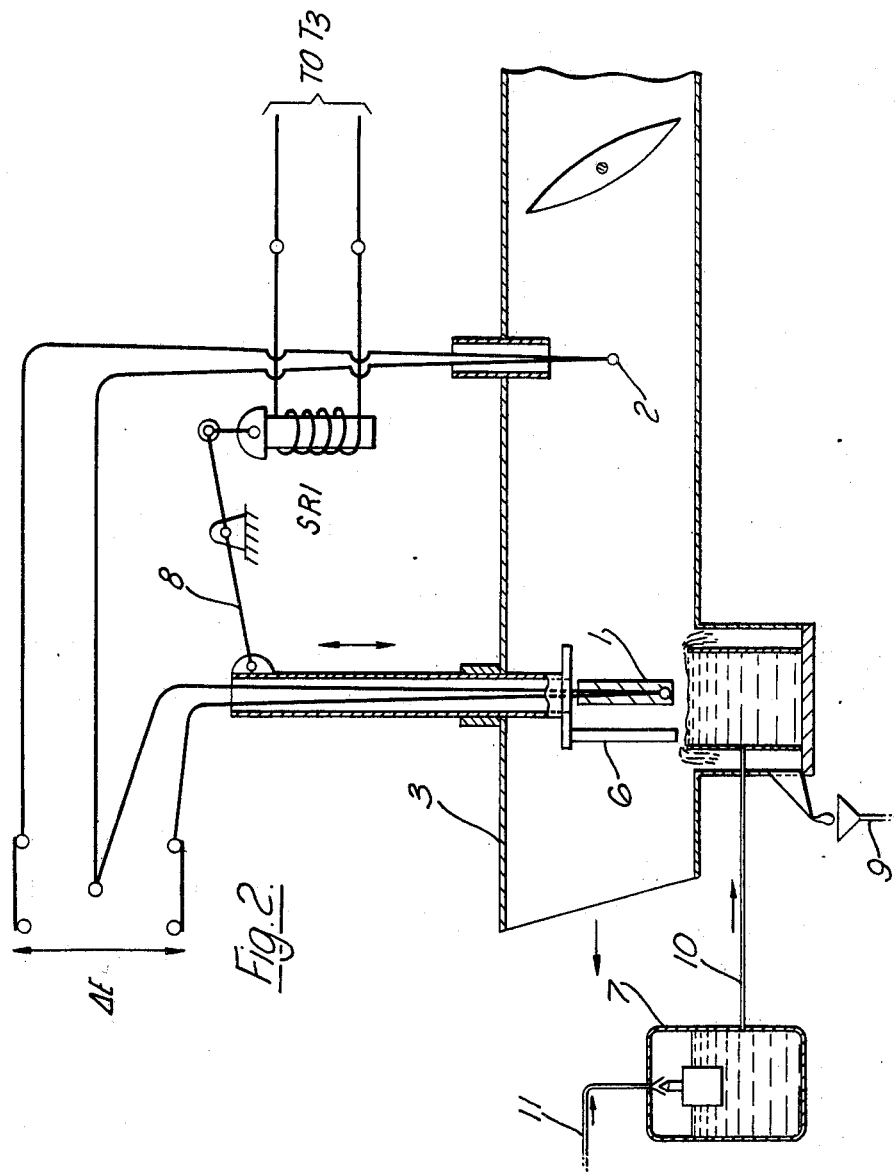

RELATIVE HUMIDITY CONTROL

The present invention relates to measurement and control of the relative humidity of exhaust air from industrial driers, the system being specifically designed for continuous operation under extreme temperature and high dust and/or other contamination of the exhaust air stream. This is in contrast to existing systems which are unable to operate continuously in high dust contamination atmospheres and/or at high temperatures.

The invention consists in apparatus for measuring and controlling the relative humidity of exhaust air from an industrial drier including means for passing a sample of exhaust air from said drier past a dry bulb and a wet bulb thermocouple electric circuit means for deriving a voltage providing a measure of the relative humidity of air in said sample from the said thermocouples, control means responsive to said voltage arranged to control the amount of exhaust air discharged from the drier to atmosphere, means to dip said wet bulb thermocouple cyclically in a container of water, a continuously cycling timer system controlling the dipping of said wet bulb thermocouple and acting to delay the application of said voltage to the said control means whereby said control means responds to said voltage only after the wet bulb thermocouple has equilibrated with the exhaust air sample after dipping and to control the duration of operation of said control means.

It is preferred that the water for the wet bulb thermocouple is derived from condensate produced in the drier and that a portion of the water is displaced at each dipping and automatically replaced.

In order that the invention may be better understood and put into practice one embodiment thereof is hereinafter described by way of example, with reference to the accompanying drawings in which FIG. 1 is a schematic diagram of a humidity controller according to the invention and FIG. 2 is a diagram illustrating in greater detail the measuring cell of the apparatus.

The measurement of relative humidity is effected in the measuring cell shown in FIG. 2 and this includes a "wet-bulb" thermocouple 1 connected to a "dry-bulb" thermocouple 2 in such a manner that the difference voltage between the two readings, $\Delta E$ provides a measure of the relative humidity of the sample of hot air leaving the dryer. No compensation for differences in the temperature of the exhaust air is included in the thermocouple circuit because this lack of compensation accentuates the response characteristics of the controller.

The "cell" for determining the relative humidity is enclosed in a tube 3 through which a sample of the exhaust air from the dryer is allowed to flow past the two thermocouples 1 and 2 and is discharged into the atmosphere. By energising the solenoid relay SR1, (by making contact B in the timer T3 FIG. 1) the "wet-bulb" thermocouple 1 is periodically immersed into the condensate container by means of the pivoted lever 8 where the "bulb" is washed to remove any dust and/or fluff contamination and is rewetted with clean condensate. During the immersion a "displacer-plunger" 6 displaces some of the condensate in the container 5 into the drain 9, ensuring that a fresh portion of clean condensate is fed into the container 5 by the float chamber 7 through the pipe 10 when the "wet-bulb" 1 and the "displacer-plunger" 6 are withdrawn and the level in the container 5 drops below that set by the float chamber. Condensate is supplied to the float chamber 7 through pipe 11 from a drier steam trap (not shown).

After immersion the "Bulb" 1 is allowed a delay time by means of the time T2 (FIG. 1) to equilibrate with the sample air stream before the resultant $\Delta E$ is fed into the automatic control system through the contact A in timer T2 (FIG. 1).

The schematic diagram of the "timer" system used (FIG. 1) shows three timers T1, T2 and T3 arranged in such a manner that when T1 times out it starts T2, which when it times out starts T3. On timing out T3 restarts timer T1 thus ensuring a continuous cycling operation of the timer system. The measuring cell output $\Delta E$ is fed into an operational amplifier OA1 and into a relay ER1 where this output from OA1 is compared to pre-set voltage fed via the variable resistor R1, calibrated in %RH units. The relay ER1 is an either-or relay which connects the 240V supply to the reversible geared motor M1 in such a manner as to either open or shut the butterfly valve BV1 depending upon whether the control voltage from OA1 is less or greater respectively than the pre-set value determined by R1.

The butterfly valve BV1 is arranged in the duct into which the exhaust stream from a drier (not shown) passes and which is open to atmosphere at its other end. Air is sampled from the duct 11 into the tube 3 via an inlet bend 12 in which an orifice is installed to restrict the air flow in the tube.

The output of the relay ER1 is allowed to reach the motor M1 via the timer T2 (contact A) only after the "wet-bulb" thermocouple has come to equilibrium with the air sample after immersion in the condensate.

In operation the measured voltage $\Delta E$ is compared with the pre-set value (of %RH) through R1 and the motor M1 opens or shuts the butterfly valve BV1 to either decrease or increase the exhaust air humidity respectively. The desired value of the relative humidity is obtained, if necessary, after a number of adjustment cycles, since the control system operates on the automatic re-set principle without any off-set error. The control of the exhaust air discharged, controls the fresh air admitted to the dryer and thus the exhaust air humidity.

The fact that the "wet-bulb" thermocouple is repeatedly dipped and a reading taken immediately after equilibration enables the apparatus to be used at higher temperatures than would otherwise be the case.

The embodiment of the invention described above is given by way of example only of the application of the invention claimed in the succeeding claims.

We claim:

1. Apparatus for measuring and controlling the relative humidity of exhaust air from an industrial drier including means for passing a sample of exhaust air from said drier past a dry bulb and a wet bulb thermocouple electric circuit means for deriving a voltage providing a measure of the relative humidity of air in said sample from the said thermocouples, control means responsive to said voltage arranged to control the amount of exhaust air discharged from the drier to atmosphere, means to dip said wet bulb thermocouple cyclically in a container of water, a continuously cycling timer system controlling the dipping of said wet bulb thermocouple and acting to delay the application of said voltage to the said control means whereby said control means responds to said voltage only after the wet bulb thermocouple has equilibrated with the exhaust air sample after dipping and to control the duration of operation of said control means.

2. Apparatus as claimed in claim 1 wherein said supply of water is provided by condensate from a drier, means being provided to cause a portion of the water in said container to be displaced at each dipping, further means being provided to replenish said container automatically prior to the next dipping.

3. Apparatus as claimed in claim 1 wherein the means to dip said wet-bulb thermocouple include a solenoid the armature of which is connected by lever means to said wet-bulb thermocouple.

4. Apparatus as claimed in claim 1 wherein said continuously cycling timer includes three timers interconnected in such a manner that as each timer times out it acts to start the next timer in the cycling sequence.

* * * * *